US00PP37115P2

(12) United States Plant Patent
Zhang

(10) Patent No.: US PP37,115 P2
(45) Date of Patent: Dec. 2, 2025

(54) ***DISTYLIUM* PLANT NAMED 'ZhDis12-16'**

(50) Latin Name: *Distylium buxifolium*
Varietal Denomination: ZhDis12-16

(71) Applicant: University of Georgia Research Foundation, Inc., Athens, GA (US)

(72) Inventor: Donglin Zhang, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 19/016,868

(22) Filed: Jan. 10, 2025

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
CPC ... A01H 5/00; A01H 5/12; A01H 5/02; A01H 6/00
See application file for complete search history.

(56) References Cited

U.S. PATENT DOCUMENTS

PP32,816 P2 * 2/2021 Lee ..... A01H 5/12 Plt./226

* cited by examiner

*Primary Examiner* — June Hwu
(74) *Attorney, Agent, or Firm* — Meunier Carlin & Curfman LLC

(57) ABSTRACT

A new and distinct cultivar of *Distylium buxifolium* plant named 'ZhDis12-16', characterized by a combination of rounded form with outward spreading, compact growing habit, bronze new foliage, and dense branches and leaves, and no notable disease and pest susceptibility.

2 Drawing Sheets

Botanical designation: *Distylium buxifolium.*
Variety denomination: 'ZhDis12-16'.

BACKGROUND

The present invention relates to a new and distinct cultivar of *Distylium*, botanically known as *Distylium buxifolium* and hereinafter referred to by the variety name 'ZhDis12-16'.

The new *Distylium buxifolium* 'ZhDis12-16' is a product of a planned breeding program conducted by the inventor at the University of Georgia in Watkinsville, GA. The objective of the *Distylium* breeding is to create new plant cultivars with compact habit, bright and colorful foliage, and short internodes and dense branches.

The new *Distylium buxifolium* 'ZhDis12-16' is a product of a selection from open pollinated seedling population of unnamed and unpatented plants of *Distylium buxifolium*. Seeds were collected on Oct. 2, 2014 from field planting of nursery stock plants in Lishui, Zhejiang, China and directly sown into the field germination beds in Hangzhou, Zhejiang, China. More than 10,000 germinated seedlings were transplanted into nursery beds on Oct. 26, 2015 for seedling plant production. On Jun. 6, 2016, a total of 16 seedlings with compact growing habit and various colorful foliage were selected and transplanted into one-gallon pots and named 'ZhDis01-16' to 'ZhDis16-16' as breeding numbers. On Oct. 26, 2016, eight better performance plants were brought to the University of Georgia with US Import Plant Permit Number P37-13-00129 for further evaluation. On Feb. 1, 2018, a total of five *Distylium* clones ('ZhDis03-16', 'ZhDis07-16', 'ZhDis12-16', 'ZhDis04-13', and 'ZhDis05-13') were delivered to a nursery in Grand Haven, MI for the restricted trial. After evaluating for five years. *Distylium buxifolium*

'ZhDis12-16' was finally selected in May 2024.

Asexual reproduction of the new *Distylium buxifolium* 'ZhDis12-16' using vegetative terminal stem cuttings has been continued in Watkinsville, GA and Spring Meadow Nursery in Grand Haven, MI since 2018. Observations of the resulting 'ZhDis12-16' progeny has shown that the unique features of this new *Distylium buxifolium* 'ZhDis12-16' are stable and reproduced true to type in successive generations.

SUMMARY OF THE INVENTION

The new *Distylium buxifolium* cultivar 'ZhDis12-16' has not been observed under all possible environmental conditions. The phenotype may vary somewhat with variations in environment and cultural practices such as temperature and light intensity without, however, any variance in genotype.

The following traits have been repeatedly observed and are determined to be the unique and distinguishing characteristics of the new *Distylium buxifolium* cultivar named 'ZhDis12-16'. In combination, these traits distinguish 'ZhDis12-16' as a new and distinct *Distylium buxifolium* cultivar:

1. Round growing form with outward spreading.
2. Dwarf habit.
3. Dense foliage and bronze new leaves.
4. Evergreen emerald green foliage all year round.
5. Clustered flowers with greyed red anthers and stigmas.
6. No fruit and seed observed.
7. No notable disease and pest susceptibility.

Plants of the new *Distylium buxifolium* differ from plants of *Distylium hybrida*—'BLDY01' (U.S. Plant Pat. No. 32,816), in the following characteristics:

1. Plants of the new *Distylium buxifolium* have sparsely stellate tomentose with new growth.
2. New foliage of the new *Distylium buxifolium* is bronze with greyed red colored leaf margin.
3. Plants of the new *Distylium buxifolium* are compact with multiple tight branches in all directions.

BRIEF DESCRIPTION OF THE PHOTOGRAPHS

The accompanying colored photographic illustration shows the overall appearance and distinct characteristics of the new cultivar of *Distylium buxifolium* 'ZhDis12-16' showing the colors as true as possible. Colors in the photographs may differ slightly from the color values cited in the detailed botanical description which accurately describes the colors of the new *Distylium buxifolium* 'ZhDis12-16'. The photographs were taken of plants grown in a poly-greenhouse in Grand Haven, Michigan in October 2024.

The photograph labeled FIG. 1 depicts a typical 4-year-old 'ZhDis12-16' plant showing canopy with round form and outward spreading.

DETAILED BOTANICAL DESCRIPTION

Figure 1:
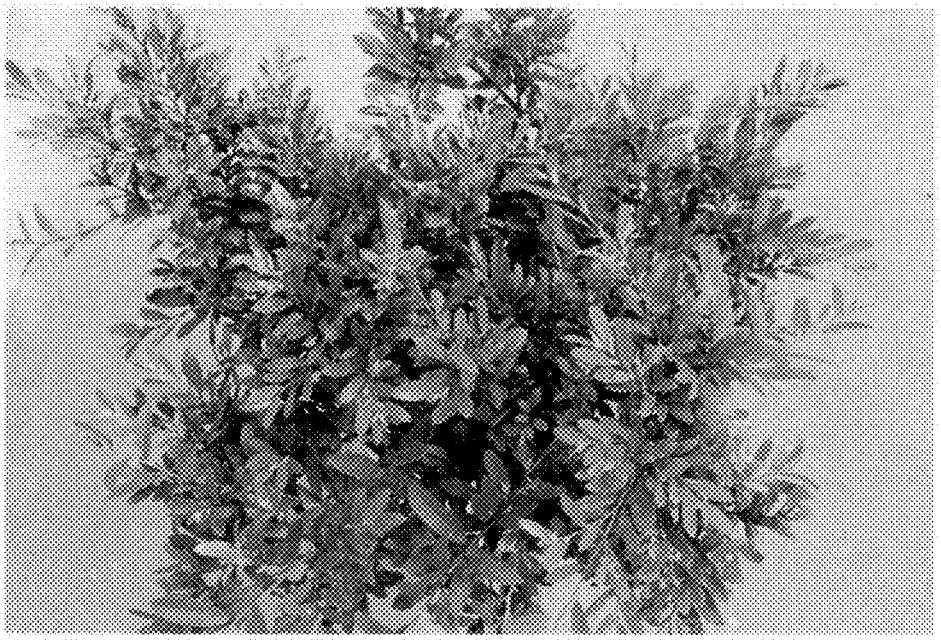
Figure 2:
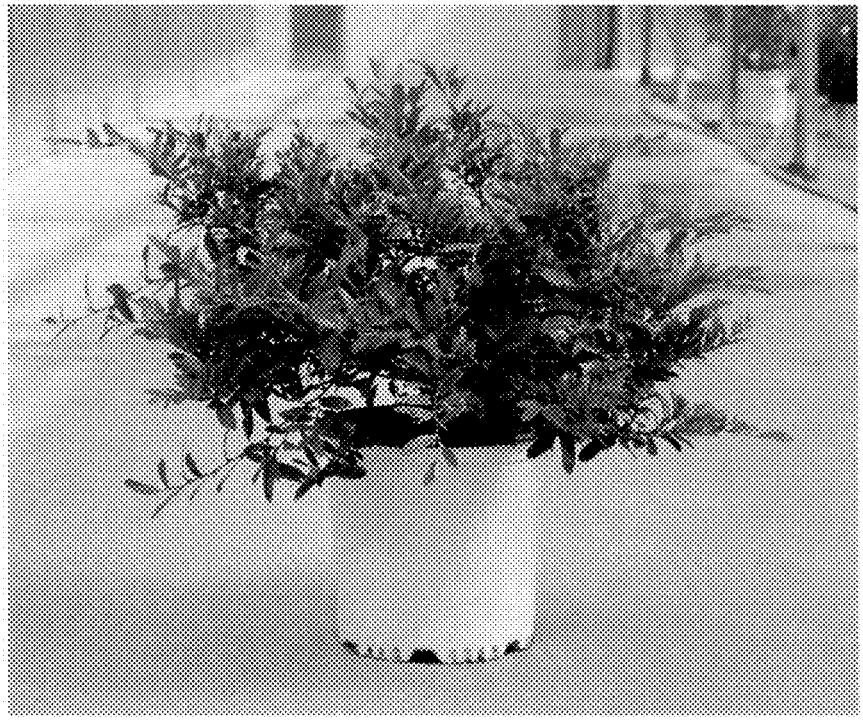
FIG. 2 depicts a typical 4-year-old 'ZhDis12-16' plant in a three-gallon container with dwarf habit.
Figure 3:
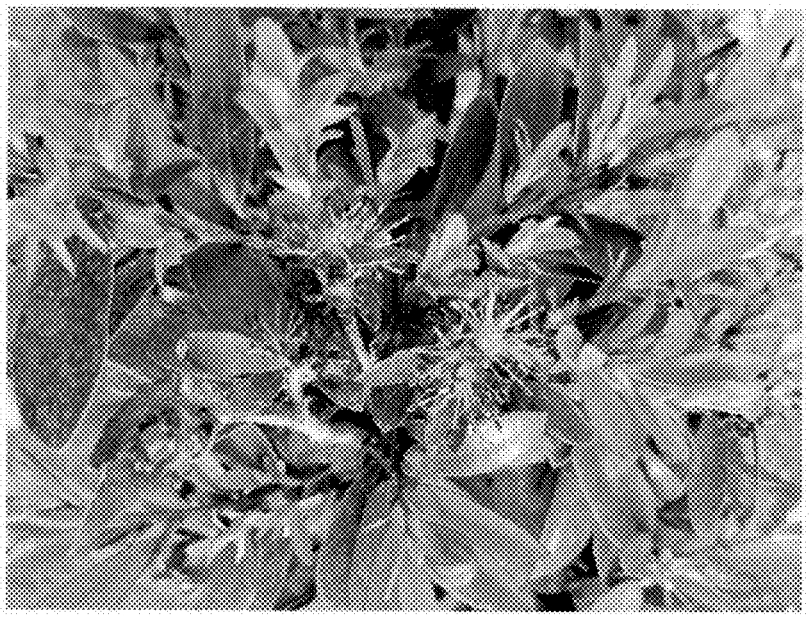
FIG. 3 depicts a typical 4-year-old 'ZhDis12-16' plant showing new growth with bronze color and male flowers.

The aforementioned photographs and following observations, measurements, and values describe plants of the *Distylium buxifolium* cultivar named 'ZhDis12-16'. Data were collected from 4-year-old plants (planted into 3-gallon containers) grown in either a horticulture farm and nursery in Watkinsville, Georgia or a poly-greenhouse in Grand Haven, Michigan. The average Georgia temperatures in the winter were approximately 67-68° F. during the day and approximately 22-23° F. during the night. The average Georgia temperatures in the summer were approximately 97-98° F. during the day and approximately 66-67° F. during the night. General light conditions are normal sunlight and numerical values represent averages of typical plant types. The data were collected in October 2024. Color names and values are from The R.H.S. Colour Chart, 6th edition, published by The Royal Horticultural Society (R.H.S.), London, UK in 2015, except where general terms of ordinary dictionary significance are used.

Botanical classification: *Distylium buxifolium* 'ZhDis12-16'.

Commercial classification: Shrub.

Parentage: Open pollination/seed propagation of unnamed and unpatented *Distylium buxifolium* clones.

Growth and propagation:

*Propagation type*.—By terminal vegetative stem cuttings.

*Growth rate*.—Hardwood stem cuttings rooted in 4-6 weeks at temperature of 75-80° F. under the mist.

*Root description*.—White fibrous roots, initiated at the portion right under the media.

*Rooting habit*.—Dense, health, freely branching root system.

Plant description:

*Form*.—Evergreen shrub, round form with outward spreading.

*Branching habit*.—Compact, basal, upward and outward.

*Bark*.—Normal gray color.

*Usage*.—Container or potted plants, border, row and mass planting.

*Vigor*.—Moderately vigorous.

*Size of plant*.—Height (cm): About 50 cm. Plant diameter and area of spread (diameter of the canopy): 101 cm.

*Stem*.—Color: New growth on upper surface: 197C and 196D. New growth on lower surface: 144A and 164B. Old growth: 199C and 199D. Length: 65 cm. Base diameter: 4 mm. Number of lateral branches: 10-15. Diameter of lateral branches: 3-3.7 mm. Lateral branch length: 16-19.7 cm. Branch angle: 30 to 70 degrees from parallel. Pubescence: None, but sparsely stellate tomentose with new growth. Shape: Rounded. Odor (of bruised stem): None. Internode length: 2 cm. Description: Loaded with lenticels. Texture and strength, mature: Very strong and rigid stems.

*Leaf*.—Leaf type: Simple/solitary. Arrangement on stem: Alternate. Leaf number: Average 12 to about 33 per lateral branch. Mature size (L×W): 4.5×1.25 cm. Leaf color (RHS): Young upper side: 168B. Young underside: 168C. Mature upper side (year-round): 147A. Mature underside (year-round): 146C. Leaf shape: Oblong. Apex: Broadly acute, sometimes obtuse. Base: Rounded. Margin: Entire, occasionally with two teeth. Pubescence: None (glabrous). Venation: Netted (reticulate). Texture: Coriaceous, smooth on both sides.

*Petiole*.—Length: 5 mm. Shape: Rounded. Diameter: 2 mm. Color (RHS): Upper side: 144C to 144A. Underside: 144C to 144A. Pubescence: Lightly pubescent. Stipules: 5 to 15 mm long, dropped immediately at maturation.

*Inflorescence*.—Arrangement: Axillary. Type: Spike. Length: 2.5 cm. Width: 1.25 cm. Number of flowers: 5 to 10.

*Flower*.—Type: Incomplete flowers, no petal. Bud: About 7 mm long, covered with dark greyish yellowish brown (N199B) to moderate yellowish brown (N199C), sessile, with an 8 mm long deciduous bract. Sepal: Inconspicuous and irregularly formed. Petal: None. Stamen: 4-5 stamens. Filament: 6 mm long, yellow green 144C in color. Anther: Oblong, 2 mm long, greyed red 180A in color. Pistil: 2, indistinguishable from style, 8 mm long. Style color: Yellow green 144C. Stigma color: Greyed red 181C.

*Fruit*.—None.

*Seed*.—None.

Weather/temperature tolerance: Plants of the new *Distylium* have been observed to tolerate temperatures from about 11° F. to about 104° F., and have been observed to be very tolerant to drought and full sun conditions.

Disease/pest resistance: Plants of the new *Distylium buxifolium* have been observed to be resistant to plants and pests common to *Distylium*.

What is claimed is:

1. A new and distinct cultivar of the *Distylium buxifolium* plant named 'ZhDis12-16' as illustrated and described herein.

* * * * *